United States Patent
Zhang et al.

(10) Patent No.: US 10,653,808 B2
(45) Date of Patent: May 19, 2020

(54) DISINFECTION APPARATUS HAVING SUBMERSIBLE UV LIGHT DEVICES

(71) Applicant: Bolb Inc., Livermore, CA (US)

(72) Inventors: Jianping Zhang, Arcadia, CA (US); Huazhong Deng, Guangdong (CN); Bin Zhang, Pleasanton, CA (US)

(73) Assignee: Bolb Inc., Livermore, CA (US)

( * ) Notice: Subject to any disclaimer, the term of this patent is extended or adjusted under 35 U.S.C. 154(b) by 21 days.

(21) Appl. No.: 15/808,905

(22) Filed: Nov. 10, 2017

(65) Prior Publication Data

US 2019/0142987 A1 May 16, 2019

(51) Int. Cl.
*A61L 2/26* (2006.01)
*A61L 2/10* (2006.01)
*C02F 1/32* (2006.01)

(52) U.S. Cl.
CPC ............... *A61L 2/26* (2013.01); *A61L 2/10* (2013.01); *C02F 1/32* (2013.01); *C02F 1/325* (2013.01); *A61L 2202/11* (2013.01); *A61L 2202/14* (2013.01); *C02F 2201/326* (2013.01); *C02F 2201/3222* (2013.01); *C02F 2201/3225* (2013.01); *C02F 2201/3227* (2013.01); *C02F 2201/3228* (2013.01); *C02F 2301/022* (2013.01); *C02F 2301/026* (2013.01); *C02F 2303/04* (2013.01)

(58) Field of Classification Search
None
See application file for complete search history.

(56) References Cited

U.S. PATENT DOCUMENTS

| | | | | |
|---|---|---|---|---|
| 2007/0086912 A1* | 4/2007 | Dowling | ............... | A01M 1/04 422/1 |
| 2007/0272877 A1* | 11/2007 | Tribelsky | ............... | A61L 2/10 250/431 |
| 2018/0244543 A1* | 8/2018 | Ochi | ............... | A61L 2/10 |

FOREIGN PATENT DOCUMENTS

WO WO-2018234816 A2 * 12/2018 ............ A61L 2/10

* cited by examiner

*Primary Examiner* — James Choi
(74) *Attorney, Agent, or Firm* — Patent Office of Dr. Chung Park

(57) ABSTRACT

Disinfection apparatus having submersible disinfection devices for disinfecting fluid. The disinfection apparatus includes: a pipe having one or more linear segments; one or more disinfection devices installed on the pipe, each of the one or more disinfection devices generating light for disinfecting fluid in a linear segment of the pipe; and a controller electrically coupled to the one or more disinfection devices and controlling the one or more disinfection devices. Another embodiment of the disinfecting apparatus includes; side and bottom walls and a lid that define an enclosed chamber; an inlet and outlet for communicating fluid to the enclosed chamber; a plurality of disinfection devices disposed on the side wall, each of the plurality of disinfection devices generating light for disinfecting fluid inside the enclosed chamber; and a controller electrically coupled to the plurality of disinfection devices and controlling the plurality of disinfection devices.

9 Claims, 13 Drawing Sheets

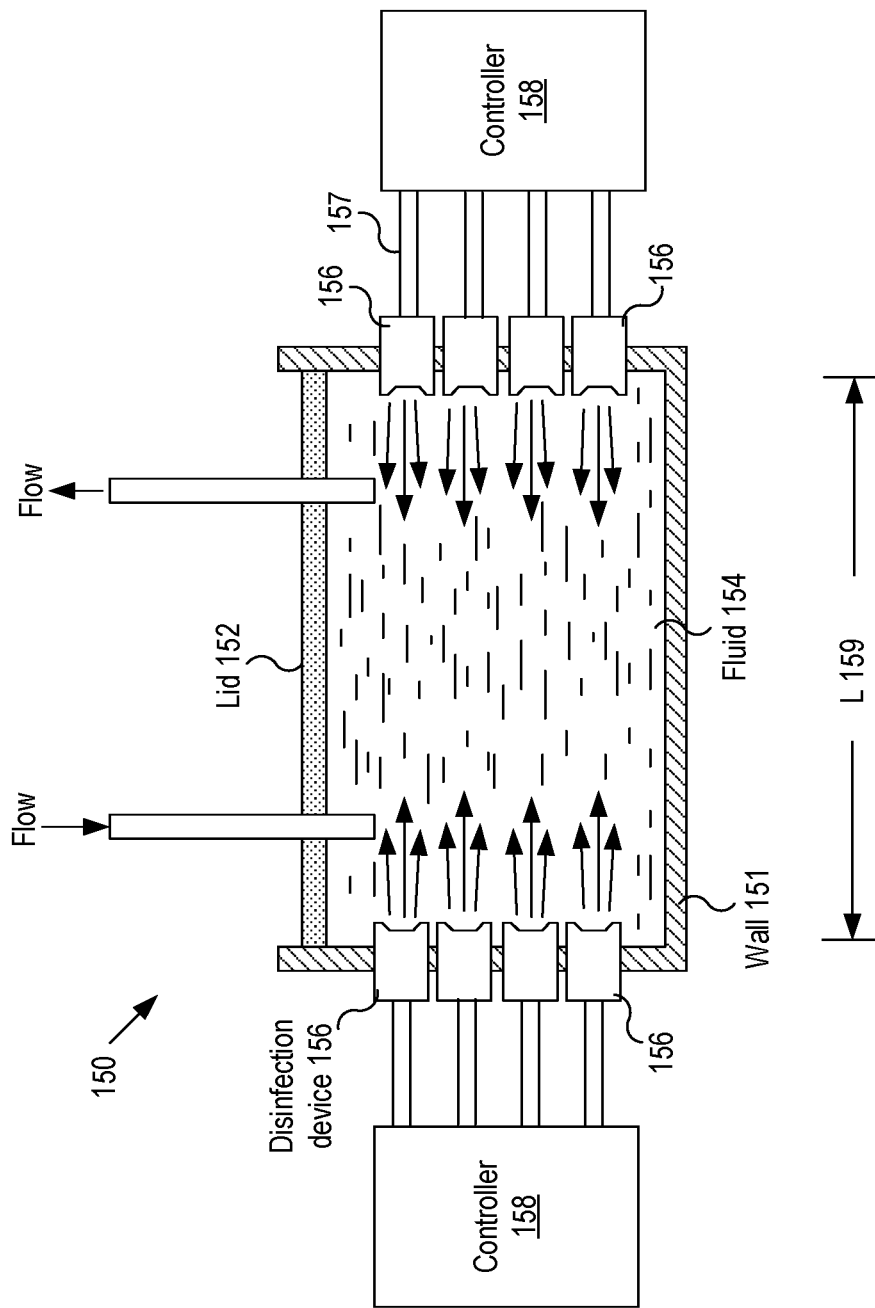

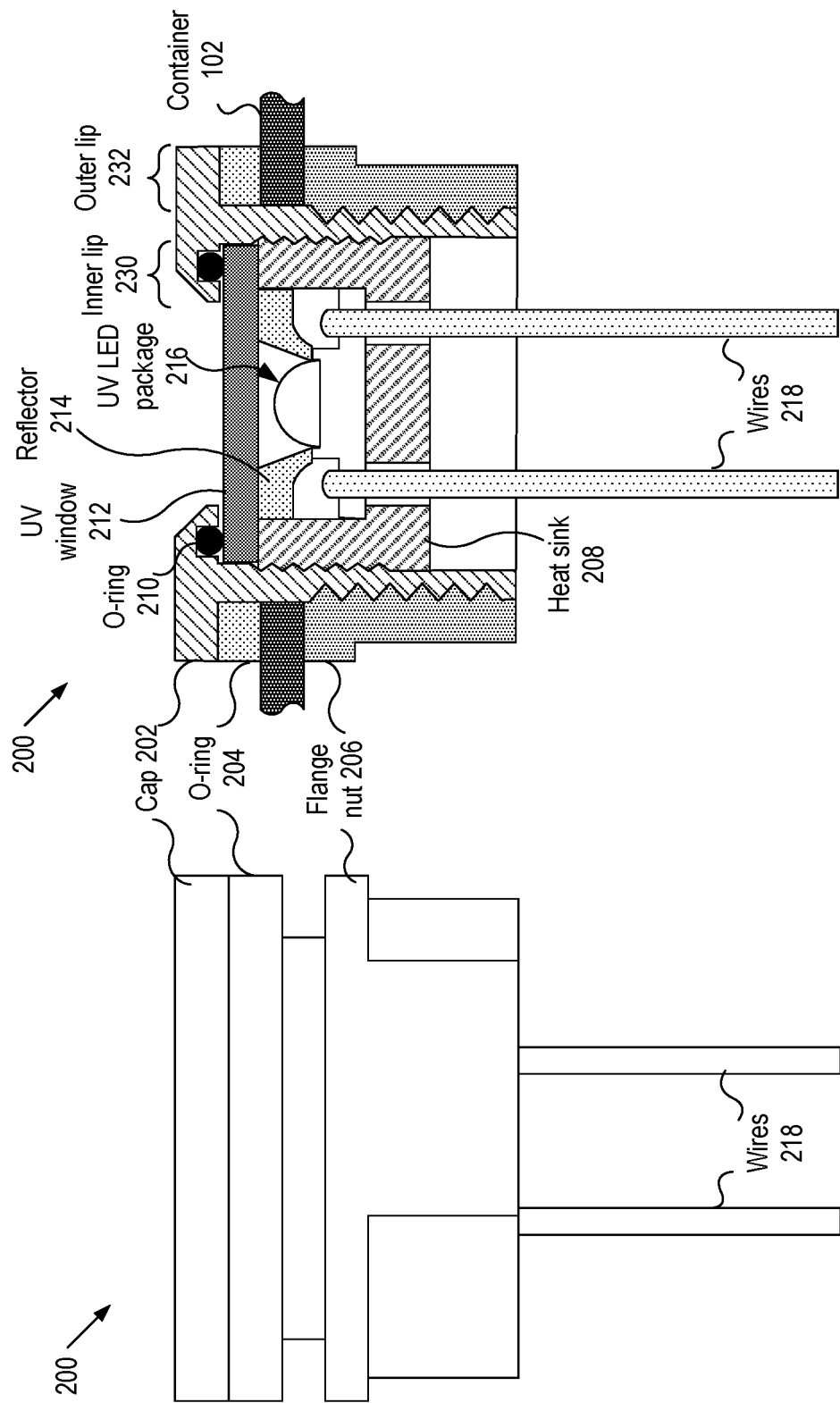

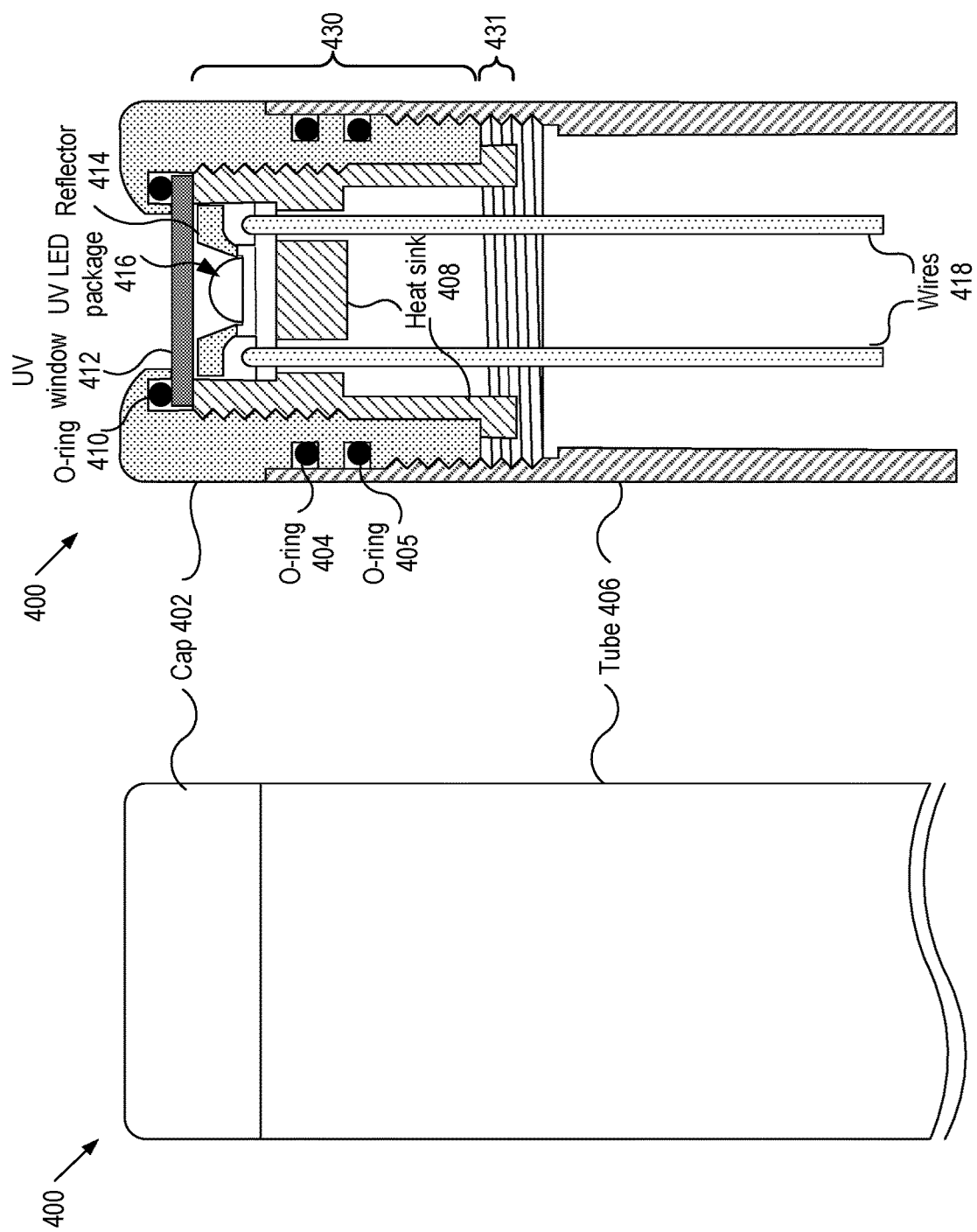

DISINFECTION APPARATUS HAVING SUBMERSIBLE UV LIGHT DEVICES

BACKGROUND

A. Technical Field

The present invention relates to fluid disinfection and ultraviolet (UV) disinfection devices, and more particularly, to fluid disinfection apparatus having submersible UV radiation disinfection devices.

B. Background of the Invention

Water and other liquids may carry infectious pathogenic microorganisms, such as bacteria, spores, viruses, and fungi, that need to be disinfected/sterilized to protect public health. UV light is known to have germicidal properties and has been developed as the disinfection light source. Specifically, the mechanism by which UV light kills microorganisms is by damaging the genetic material, the deoxyribonucleic acid (DNA), of the microorganisms and wavelengths between 200-300 nm have been shown to initiate a photoreaction between adjacent pyrimidines.

In general, different microbes have different UV disinfection dosages. When using the conventional low-pressure mercury lamp UV emissions at 254 nm, the National Sanitation Foundation (NSF) Standard 55-1991 Ultraviolet Microbiological Water Treatment Systems demand the NSF failsafe set-point dosage for Class A systems UV water treatment system is 40 mJ/cm$^2$, and International Water-Guard designs its Class A units to operate at a minimum dosage of 40 mJ/cm$^2$ as well. Class A systems are those designed to disinfect water contaminated by micro-organisms like bacteria and viruses, but not water with an obvious contamination source such as raw sewage, nor are they designed to convert wastewater to safe drinking water. Class B systems are intended to provide supplemental treatment of drinking water that has been tested by health authorities and deemed acceptable for human consumption. The NSF dosage requirement for Class B systems using 254 nm emission is 16 mJ/cm$^2$. Use of 265-275 nm UV emissions for disinfection, which have the maximal UV germicidal effect, can reduce the required dosage for the same germicidal effect as compared to the use of 254 nm UV light. UV emissions at 265 nm and in the range of 200 nm to 400 nm can be generated by group III nitride semiconductor UV light emitting diodes (LEDs).

To design an efficient UV disinfection apparatus for fluids and liquids with targeted UV dosage, various aspects have to be taken into consideration. Firstly, UV radiations can only penetrate a liquid to a certain depth, and as such, any liquid that is farther away from the radiation source than the penetration depth is not sufficiently irradiated. Secondly, UV radiation or UV light can be readily absorbed by fluid container's surface, since most solids have very small UV reflectivity. This requires optical designs to minimize UV/container encounter. Thirdly, UV dosage delivered is proportionally to UV exposure duration time. An efficient design thus will maximize UV duration time, without merely relying on increasing UV light source output power. Thus, there is a need for fluid disinfection apparatuses having submersible UV light devices that address the above identified considerations.

SUMMARY OF THE DISCLOSURE

In one aspect of the present invention, a disinfection apparatus includes: a pipe having one or more linear segments; one or more disinfection devices installed on the pipe to be partially submersible in fluid, each of the one or more disinfection devices being configured to generate light for disinfecting fluid in a linear segment of the pipe; and a controller electrically coupled to the one or more disinfection devices and configured to control the one or more disinfection devices.

In another aspect of the present invention, a disinfection apparatus includes: side and bottom walls configured to hold liquid; a lid disposed on the side wall to thereby define an enclosed chamber surrounded by the side wall, the bottom wall and the lid; an inlet for introducing liquid into the enclosed chamber; an outlet for discharging liquid from the enclosed chamber; a plurality of disinfection devices disposed on the side wall to be partially submersible in liquid, each of the plurality of disinfection devices being configured to generate light for disinfecting liquid inside the enclosed chamber; and a controller electrically coupled to the plurality of disinfection devices and configured to control the plurality of disinfection devices.

BRIEF DESCRIPTION OF THE DRAWINGS

References will be made to embodiments of the invention, examples of which may be illustrated in the accompanying figures. These figures are intended to be illustrative, not limiting. Although the invention is generally described in the context of these embodiments, it should be understood that it is not intended to limit the scope of the invention to these particular embodiments.

FIG. 1F shows a cross sectional view of a container having multiple UV disinfection devices according to embodiments of the present disclosure.

FIG. 2A shows a side view of a UV disinfection device according to embodiments of the present disclosure.

FIG. 2B shows a cross sectional view of the UV disinfection device in FIG. 2A.

FIG. 4A shows a side view of a UV disinfection device according to embodiments of the present disclosure.

FIG. 4B shows a cross sectional view of the UV disinfection device in FIG. 4A.

DETAILED DESCRIPTION OF THE PREFERRED EMBODIMENTS

In the following description, for the purposes of explanation, specific details are set forth in order to provide an understanding of the disclosure. It will be apparent, however, to one skilled in the art that the disclosure can be practiced without these details. One skilled in the art will recognize that embodiments of the present disclosure, described below, may be performed in a variety of ways and using a variety of means. Those skilled in the art will also recognize additional modifications, applications, and embodiments are within the scope thereof, as are additional fields in which the disclosure may provide utility. Accordingly, the embodiments described below are illustrative of specific embodiments of the disclosure and are meant to avoid obscuring the disclosure.

A reference in the specification to "one embodiment" or "an embodiment" means that a particular feature, structure, characteristic, or function described in connection with the embodiment is included in at least one embodiment of the disclosure. The appearance of the phrase "in one embodiment," "in an embodiment," or the like in various places in the specification are not necessarily all referring to the same embodiment.

Figure 1A:
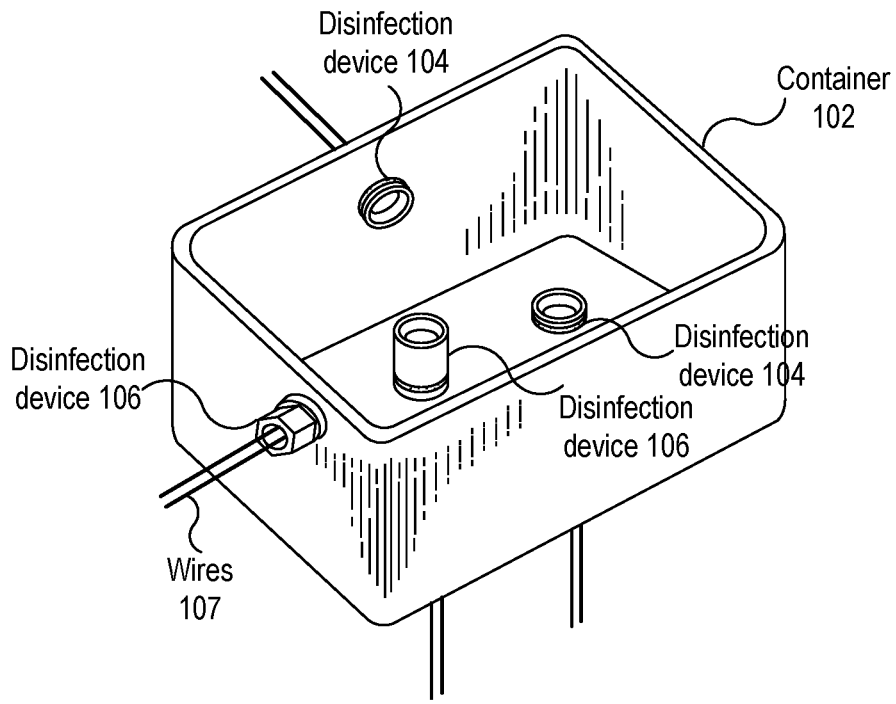
FIG. 1A shows a perspective view of a liquid container with one or more UV disinfection devices according to embodiments of the present disclosure.

FIG. 1A shows a perspective view of a container 102 with one or more UV disinfection devices (or, shortly devices) 104 and 106 according to embodiments of the present disclosure. As depicted, the container 102 may hold liquid therein and the liquid may be disinfected by the UV disinfection devices 104 and 106. In FIG. 1A, only four UV disinfection devices are shown. However, it should be apparent to those of ordinary skill in the art that any suitable number of disinfection devices may be mounted on the wall of the container 102. Also, it should be apparent to those of ordinary skill in the art that the UV disinfection devices may be mounted in other locations, such as lid, of the container 102. In embodiments, each of the disinfection devices 104 and 106 may include wires 107 for communicating electrical signals to a suitable controller (not shown in FIG. 1A) or a power source. In the present application, the disinfection devices are described to contain UV light emitting diodes (LEDs) that generate disinfecting UV light, even though any other suitable light sources that generate disinfecting light may be used in place of the UV LEDs.

In FIG. 1A, the container 102 may include an inlet and an outlet (not shown in FIG. 1A), where the liquid to be disinfected may flow into the container through the inlet and the disinfected liquid may flow out of the container through the outlet. In embodiments, the container 102 may not have any inlet or outlet, such as fish tank, and, instead, may have a mechanism that generate flow therein.

As depicted in FIG. 1A, the UV disinfection devices 104 and 106 may be submersible in liquid, and as such, the UV disinfection devices 104 and 106 may include sealing mechanisms, such as o-rings, that prevent the liquid from leaking into the devices or through the gap between the devices and the wall of the container 102.

Figure 1B:
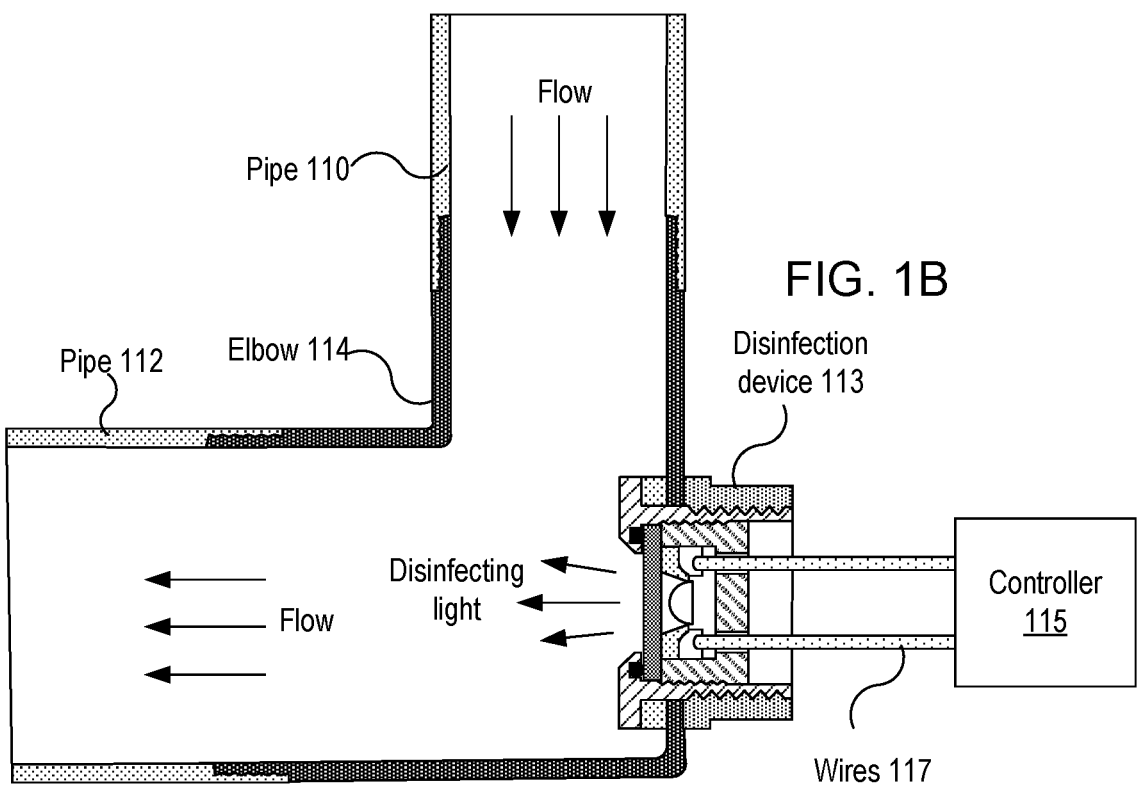
FIG. 1B shows a cross sectional view of a pipe elbow with a UV disinfection device according to embodiments of the present disclosure.

FIG. 1B shows a cross sectional view of a pipe elbow 114 with a UV disinfection device 113 according to embodiments of the present disclosure. As depicted, the pipe elbow 114 may have male threads that engage the female threads of pipes 110 and 112. As depicted in FIG. 1B, the UV disinfection device 113, which may be similar to 104 or 106, may be submersible in liquid, and as such, the UV disinfection device 113 may include sealing mechanisms, such as o-rings, that prevent the liquid from leaking into the devices or through the gap between the devices and the wall of the pipe elbow 114. In embodiments, the intensity of disinfecting light, which may be preferably, but not limited to, collimated or semi-collimated, from the disinfection device 114 may be controlled by a controller 115 that is coupled to the devices by the wires 117.

Figure 1C:
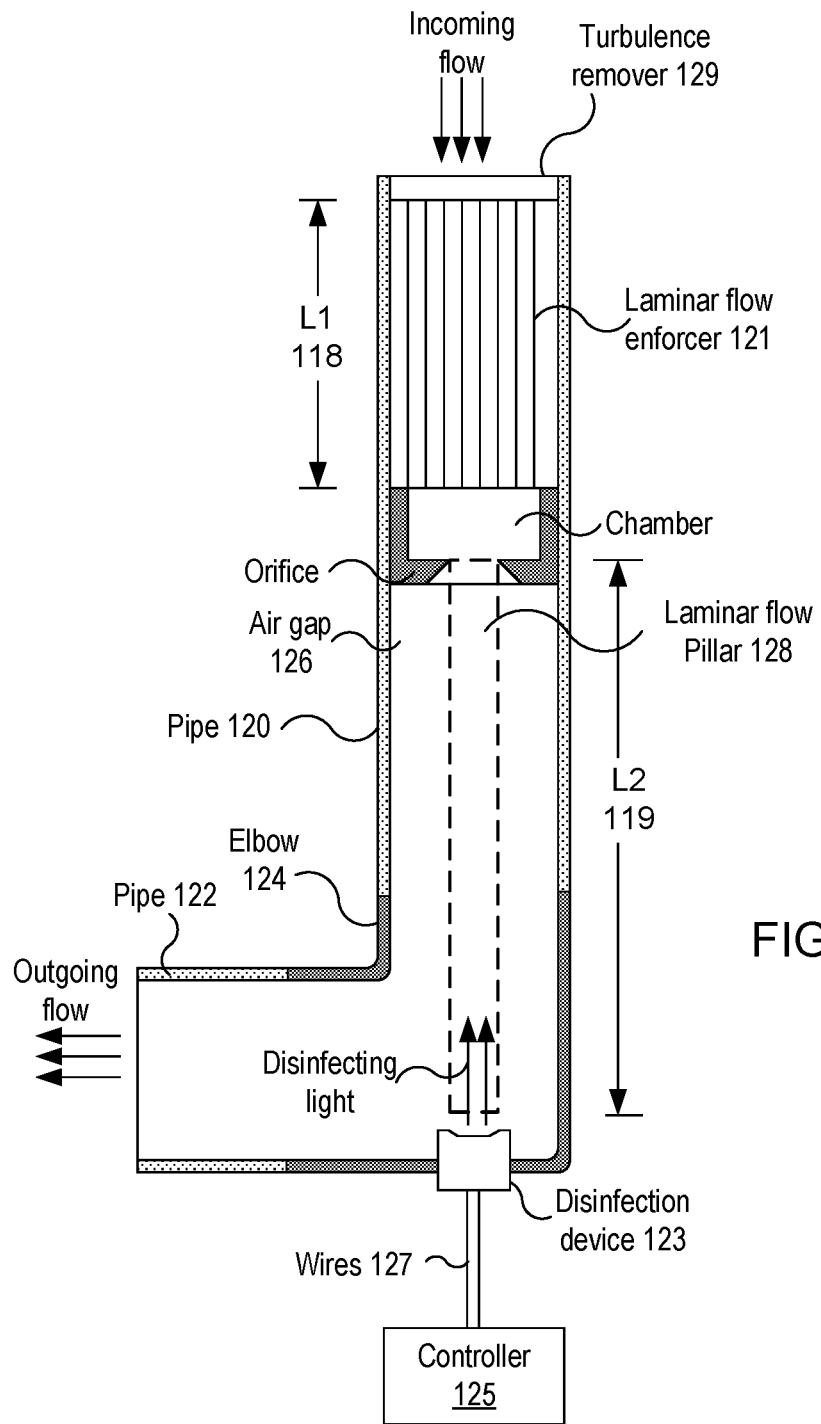
FIG. 1C shows a cross sectional view of a pipe elbow with a UV disinfection device according to embodiments of the present disclosure.

FIG. 1C shows a cross sectional view of a pipe elbow 124 with a UV disinfection device 123 according to embodiments of the present disclosure. In embodiment, the pipe elbow 124 may be detachably secured to the pipes 120 and 122 by suitable fastening mechanism, such as threads. As depicted in FIG. 1C, the UV disinfection device 123, which may be similar to 104 or 106, may be submersible in liquid, and as such, the UV disinfection device 123 may include sealing mechanisms, such as o-rings, that prevent the liquid from leaking into the devices or through the gap between the devices and the pipe elbow 124. In embodiments, the intensity of disinfecting light, which may be preferably, but not limited to, collimated or semi-collimated, from the disinfection device 123 may be controlled by a controller 125 that is coupled to the devices by the wires 127.

As shown in FIG. 1C, the disinfection device 123 may face against the incoming flow. In embodiments, the flowing fluid may be turned into a laminar flow pillar 128 by a laminar flow enforcer 121. In embodiments, on top of the laminar flow enforcer 121, there may be a turbulence remover 129 that may remove or reduce turbulence within the incoming flow. In embodiments, the turbulence remover 129 may include a layer or many layers of coarse fluid filters radially disposed, and each coarse fluid filter may be a sediment filter or a particle filter with micro-mesh.

In embodiments, the laminar flow enforcer 121 may include densely packed, straight, parallel small tubes of lengths exceedingly larger than their cross-sectional dimensions. For instance, the length-diameter ratio of the tubes may be in the range of 10-100. In embodiments, the cross section of each tube may have a suitable geometrical shape, such as circle, rectangle or square. The radial dimension of each tube may be in the range of 0.05-0.3 inch (such as 0.1 inch), and its length, L1 118, may be in the range of 0.6-8 inch (such as 1, 4, or 7.5 inch). In an embodiment, the diameter of the tube is 0.1 inch and the length of the tube is 5 inch. In embodiments, all the tubes have the same cross-sectional shape and dimension. The space, if any, between the laminar flow enforcer 121 and the pipe 120 may be sealed so that no fluid flows therethrough.

In embodiments, the laminar flow enforcer 121 may divide the fluid flow into numerous sub-flows and enforce these sub-flows to flow straight and in parallel to each other, to thereby make it possible to turn the fluid flow into a laminar flow pillar 128, substantially free of turbulence and bubbles. As shown in FIG. 1C, there is a chamber below the laminar flow enforcer 121 to collect all the parallel sub-flows and build up fluid pressure. On the chamber wall directly facing the disinfection device 123 there is an orifice acting as nozzle to inject laminar flow pillar 128 to disinfection device 123. In embodiments, there may be an air gap 126 between the fluid laminar flow pillar 128 and the inner surface of the pipe 120. In embodiments, the air gap 126 may be formed by one or more of the following mechanisms: 1) the cross-section of laminar flow pillar 128 as defined by the orifice is less than the pipe cross-section; 2)

the surface tension of the fluid; 3) the gravitational pull is parallel to the laminar flow pillar 128; and 4) the flow is laminar.

In embodiments, the length, L2 119, of the laminar flow pillar 128, which is the distance between the orifice on the chamber wall and the light emitting surface of the disinfection device 123, may be long enough to allow for sufficient UV light dosage delivered to the laminar flow pillar 128. In embodiments, L2 119 may be in the range of 10-100 cm, such as 20-50 cm or 30-70 cm. In embodiments, the air gap 126 surrounding the laminar flow pillar 128 may possess the refractive index equal to 1.0, which may be smaller than that of the laminar flow pillar 128, and provide a total internal reflection mechanism to confine the collimated or quasi-collimated UV light traveling in the laminar flow pillar 128. In embodiments, this internal reflection at the boundary between the air gap 126 and the laminar flow pillar 128 may reduce or even totally eliminate the possibility of UV light/pipe wall encounter, maximizing the UV dosage delivery to the fluid to be disinfected.

Figure 1D:
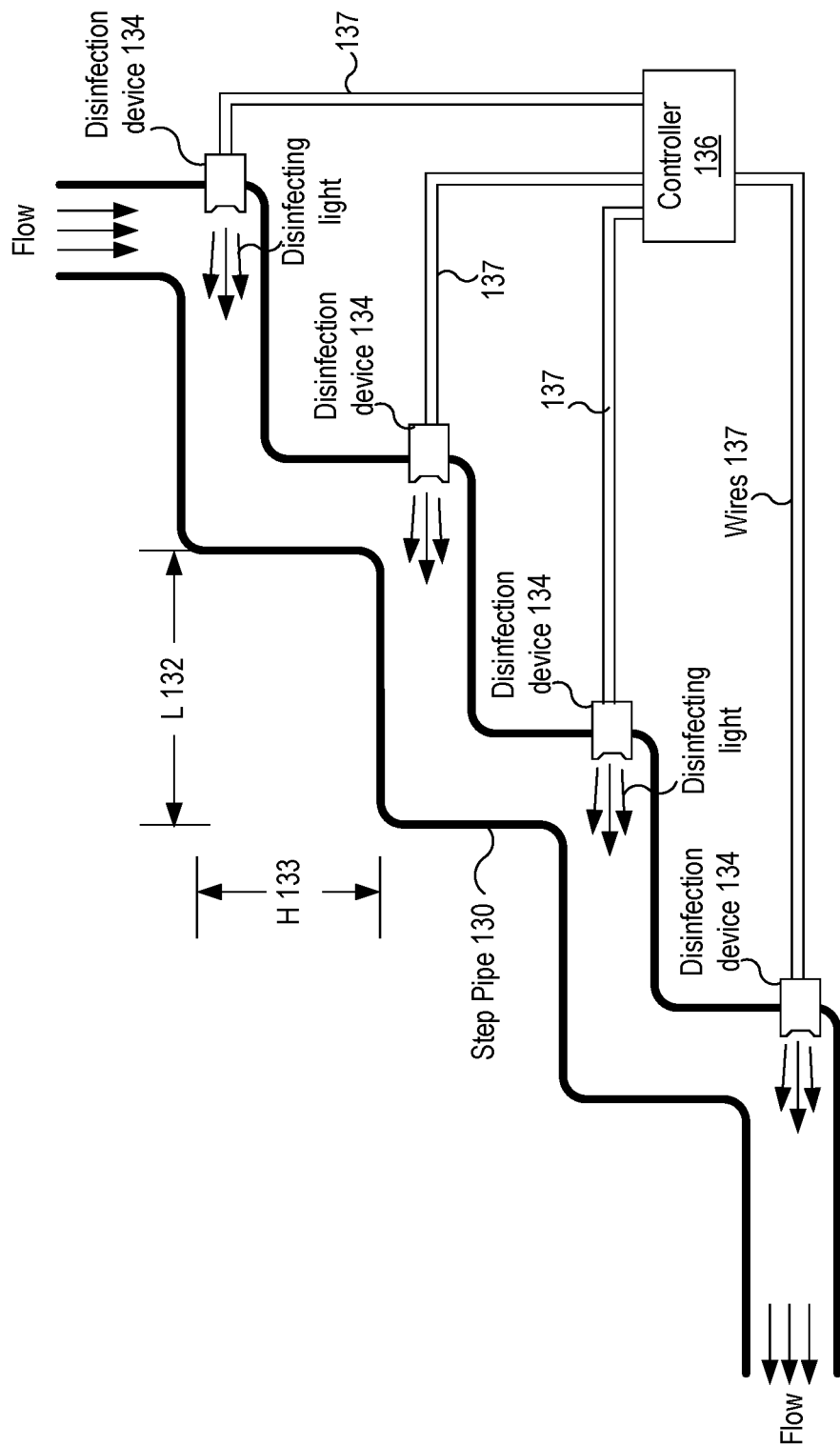
FIG. 1D shows a cross sectional view of a pipe having multiple UV disinfection devices according to embodiments of the present disclosure.

FIG. 1D shows a cross sectional view of a pipe 130 having multiple UV disinfection devices 134 according to embodiments of the present disclosure. As depicted, the pipe 130 may have multiple bending points to form multiple steps and each UV disinfection device 134 may generate the disinfecting light that disinfects the fluid flowing through a corresponding linear segment of the pipe. The disinfecting light generated by device 134 is preferred to be collimated or quasi-collimated light, parallel to the flowing fluid within the linear segment of the pipe to maximize the UV dosage delivery to the fluid and minimize light/pipe encounter. In embodiments, the pipe 130 may be a monolithic body and have multiple holes, where the UV disinfection devices 134 may be submersible and installed in the holes. In alternative embodiments, the pipe 130 may include multiple linear pipes and elbows, and each pipe elbow may include a hole for installing a UV disinfection device 134, as shown in FIG. 1B or 1C.

In general, the disinfecting light may be absorbed by the fluid in the pipe. In embodiments, the length L 132 and height 133 may be adjusted according to the fluid's absorption coefficient, maximizing the UV dosage delivered to the fluid. For instance, the length L 132 may range 2-100 cm, and the height H 133 may range from 2-10 cm. In embodiments, the intensity of disinfecting light from each disinfection device 134 may be controlled by a controller 136 that is coupled to the devices by the wires 137. In embodiments, the intensity of the disinfecting light from each disinfection device and/or the total dosage of the disinfecting light delivered to the fluid by the multiple disinfection devices 134 may be increased if the fluid has a higher absorption coefficient or the flow rate is increased.

Figure 1E:
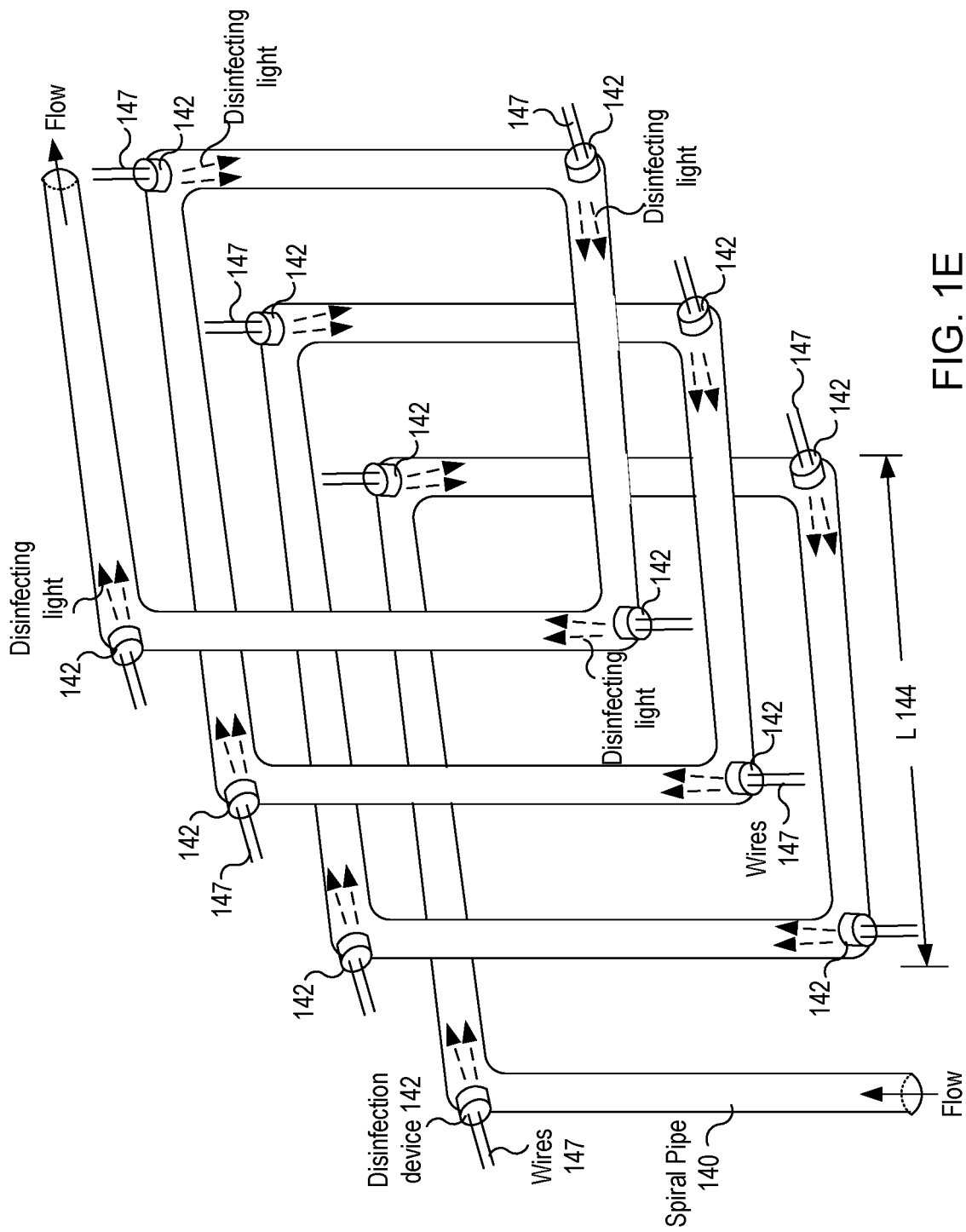
FIG. 1E shows a perspective view of a pipe having multiple UV disinfection devices according to embodiments of the present disclosure.

FIG. 1E shows a perspective view of a pipe 140 having multiple UV disinfection devices 142 according to embodiments of the present disclosure. As depicted, the pipe 140 may have multiple bending points to form a spiral shape and each UV disinfection device 142 may generate the disinfecting light that disinfects the fluid flowing through a corresponding linear segment of the pipe. The disinfecting light generated by device 142 is preferred to be collimated or quasi-collimated light, parallel to the flowing fluid within the linear segment of the pipe to maximize the UV dosage delivery to the fluid and minimize light/pipe encounter. In embodiments, the pipe 140 may be a monolithic body and have multiple holes, where the UV disinfection devices 142 may be submersible and installed in the holes. In alternative embodiments, the pipe 140 may include multiple linear pipes and elbows, and each pipe elbow may include a hole for installing a UV disinfection device 142, as shown in FIG. 1B.

In general, the disinfecting light may be absorbed by the fluid in the pipe. In embodiments, the length L 144 of each linear segment of the pipe may be adjusted according to the fluid's absorption coefficient, maximizing the UV dosage delivered to the fluid. For example, L 144 may be in the range of 5 to 50 cm. In embodiments, the intensity of disinfecting light from each disinfection device 142 may be controlled by a controller (not shown in FIG. 1E) that is electrically coupled to the device via the wires 147. In embodiments, the intensity of the disinfecting light from each disinfection device and/or the total dosage of the disinfecting light delivered to the fluid by the multiple disinfection devices 142 may be increased if the fluid has a higher absorption coefficient or the flow rate is increased. For the embodiments shown in FIGS. 1D and 1E, more or less linear segments with disinfection light sources can be applied, for larger or smaller dosage delivery to the fluid to be disinfected. It is noted that the pipes in FIGS. 1A-1E may have various cross-sectional shapes, such as circle, rectangle, ellipse, square so on.

FIG. 1F shows a cross sectional view of a container 150 having multiple UV disinfection devices 156 according to embodiments of the present disclosure. As depicted, the container 150 may include a wall 151 and a lid 152 that define a chamber for holding the fluid 154. The container 150 may further include inlet and outlet pipes may pass through the lid 152. In embodiments, the wall 151 may include multiple holes where the disinfection devices 156 may be installed.

In embodiments, the chamber length, L 159, may be determined by the fluid's absorption coefficient and targeted dosage of the disinfecting light delivered to the fluid 154. For example, L 159 may be in the range of 5 to 50 cm. In embodiments, the intensity of disinfecting light from each disinfection device 156 may be controlled by one or more controllers 158 coupled to the device via the wires 157. In embodiments, the intensity of the disinfecting light from each disinfection device and/or the total dosage of the disinfecting light delivered to the fluid by the multiple disinfection devices 156 may be increased if the fluid has a higher absorption coefficient or the flow rate is increased.

It is noted that the disinfection devices in FIGS. 1A-1F may emit collimated or quasi-collimated disinfecting light for disinfecting the fluid. Also, in embodiments, each disinfection device may be submersible in the liquid, easily mounted to and dismounted from the containers/pipes by a pair of threads, and be individually replaceable, which facilitates the maintenance of the devices. Various embodiments of the disinfection devices in FIGS. 1A-1F are described in conjunction with FIGS. 2A-5C.

Figure 2C:
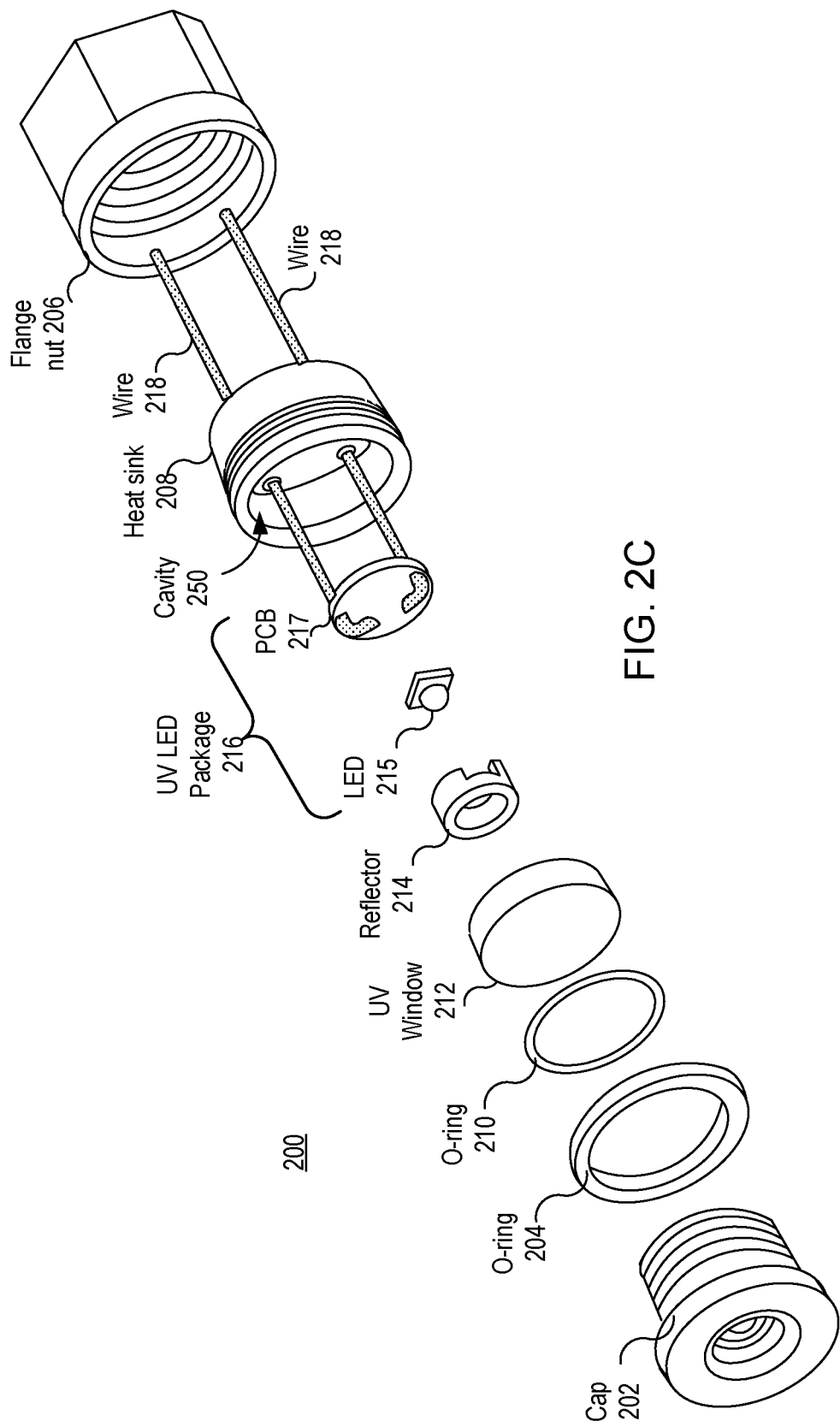
FIG. 2C shows an exploded perspective view of the UV disinfection device in FIG. 2A.

FIG. 2A shows a side view of a UV disinfection device 200 according to embodiments of the present disclosure. FIG. 2B shows a cross sectional view of the UV disinfection device 200 in FIG. 2A. FIG. 2C shows an exploded perspective view of the UV disinfection device 200 in FIG. 2A. As depicted, the UV disinfection device 200, which may be similar to the device 104, may include: a cap 202 having a hollow cylindrical body, an inner lip 230 disposed along a top inner rim of the body and including an o-ring groove, and an outer lip 232 disposed along a top outer rim of the body, the body including a first thread formed on an inner side surface of the body and a second thread formed on an outer side surface of the body; a heat sink 208 being a hollow cylinder that has an open top end, a closed bottom end to thereby define a space (cavity) 250 inside the hollow cylinder, and a third thread formed on an outer side surface and engaging the first thread of the cap; a UV light source package (such as UV LED package) 216 disposed inside the space (cavity) 250 and generating UV light; a UV reflector 214 that reflects the UV light generated by the UV light source package 216; a first o-ring 210 seating on the o-ring groove formed in the inner lip 230; a UV window disposed on the open top end of the heat sink 208 and having a top surface that is in direct contact with the first o-ring.

When the heat sink 208 is secured into the cap 202 by engaging the first thread into the third thread, the top surface of the heat sink 208 may push the window 212 upwardly and the top surface of the window 212 may compress the first o-ring 210 so that the first o-ring 210 may prevent the liquid from leaking into the cavity 250. (Hereinafter, the term thread and fastening mechanism are used interchangeably.)

In embodiments, the UV disinfection device 200 may further include: a flange nut 206 having a fourth thread that engages the second thread of the cap 202 and being hexagonal in shape; and a second o-ring 204. To mount the device 200 on the wall of the container 102, the fourth thread of the flange nut 206 may be screwed into the second thread of the cap 202. Also, upon turning the flange nut 206 relative to the cap 202, the second o-ring 204 may be compressed by the wall of the container 102 and the outer lip 232 of the cap 202 so that the second o-ring may prevent the liquid from leaking through the gap between the device 200 and the wall of the container 102.

In embodiments, the heat sink 208 may dissipate the heat energy generated by the UV light source package 216, i.e., the heat sink may transfer the heat energy from the UV light source package 216 to the cap 202, and the cap 202 in turn may discharge the heat energy into the liquid. In embodiments, the heat sink 208 may be formed of material that has a high heat transfer coefficient, such as copper, stainless steel, aluminum, or other suitable metal. In embodiments, the cap 202 may be formed of metal, such as copper, stainless steel, and aluminum. In embodiments, the flange nut 206 may be formed of metal, such as copper, stainless steel, and aluminum. It is noted that the heat energy generated by the UV light source package 216 may be transferred from the heat sink 208 to the flange nut 206, and the flange nut 206 may also discharge the heat energy to the container 102 or ambient atmosphere.

In embodiments, the UV reflector 214 may reflect the UV light from the UV light source package 216 so that the UV light may be focused into collimated or quasi-collimated light beam and steered toward the liquid. In embodiments, the UV reflector 214 may be formed of highly reflective material, such as aluminum, or the inner surface of the UV reflector 214 may be coated with a reflecting material.

In embodiments, the UV window 212 may be formed of material, such as quartz, fused silica, or sapphire, that is transparent to the UV light generated by the UV light source package 216.

In embodiments, the UV light source package may include a printed circuit board (PCB) 217 and a light emitting diode (LED) 215 mounted on the PCB. In embodiments, a pair of electrical wires 218 may be electrically coupled to the PCB 217 so that the electrical signals may be transmitted to the PCB 217 from outside the device 200. It should be apparent to those of ordinary skill in the art that the UV light source package 216 may include a suitable light source other than the LED 215.

It is noted that the UV disinfection device 200 has two o-rings (i.e., two sealing mechanisms) that ensure a tight liquid proof seal when the device is mounted on the container wall and a portion of the device is submerged in the liquid. In embodiments, the first o-ring 210 may prevent the liquid from leaking into the space (cavity) in the heat sink 208, i.e., the first o-ring 210 may protect the electrical circuit of the UV light source package 216 from damages by the liquid.

In embodiments, the heat energy generated by the UV light source package 216 may be efficiently dissipated into the liquid through the heat sink 208 and the cap 210. As such, in embodiments, the cooling mechanism may protect the device from thermal damages, allowing application of the device 200 to high power disinfections.

In general, the direct contact between the liquid and the device 200 may lead to fouling of the UV window 212 and, thus, the device 200 need to be easily mounted to and dismounted from the container 102 for maintenance purposes. In embodiments, the UV disinfection device 200 may be mounted to and dismounted from the wall of the container 102 by simply turning the flange nut 206 relative to the cap 202, reducing the effort for maintenance of the device 200. In embodiments, the outer diameter of the cap 202 may be about 18 mm.

Figures 3A, 3B:
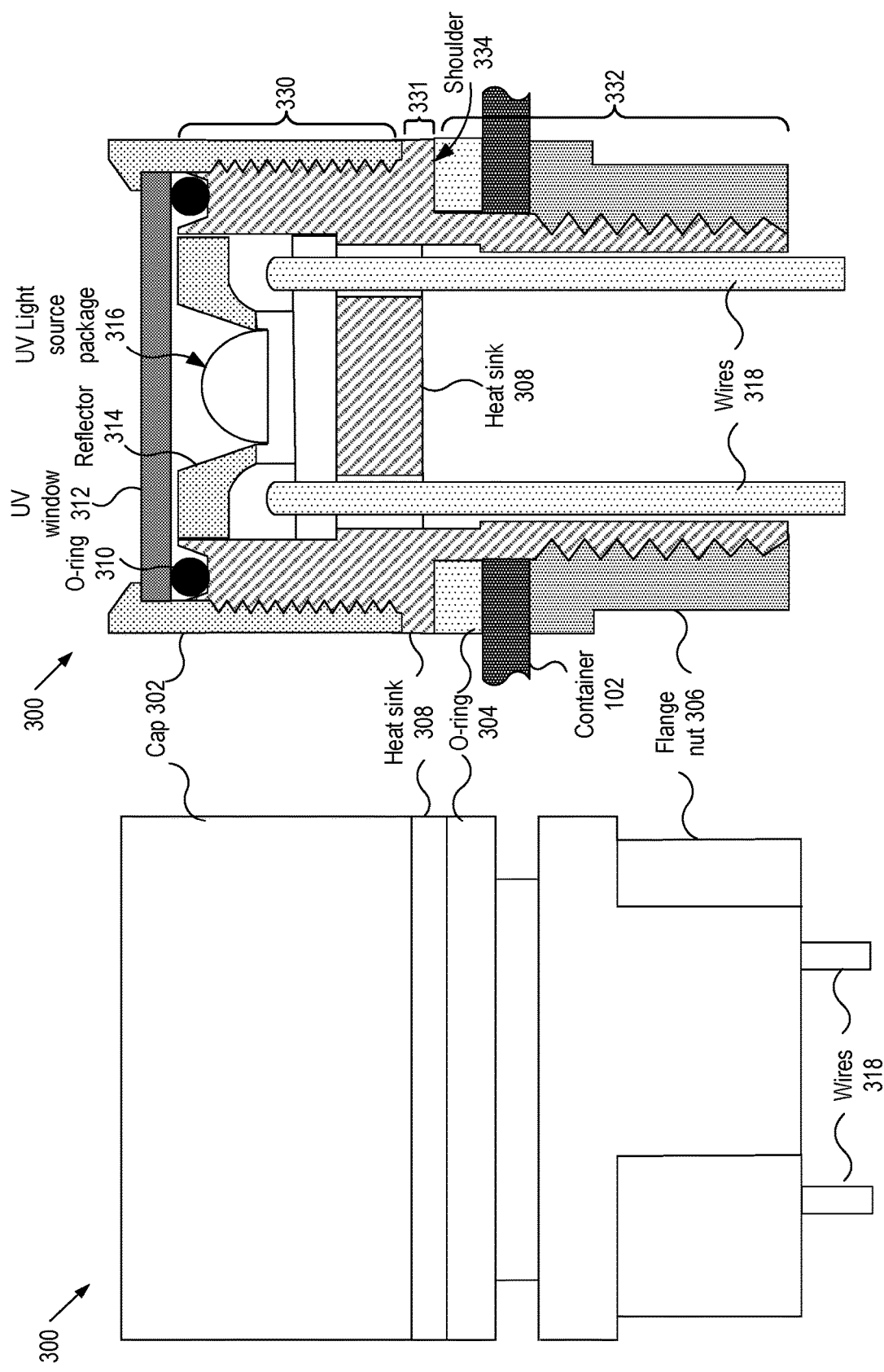
FIG. 3A shows a side view of a UV disinfection device according to embodiments of the present disclosure.
FIG. 3B shows a cross sectional view of the UV disinfection device in FIG. 3A.
Figure 3C:
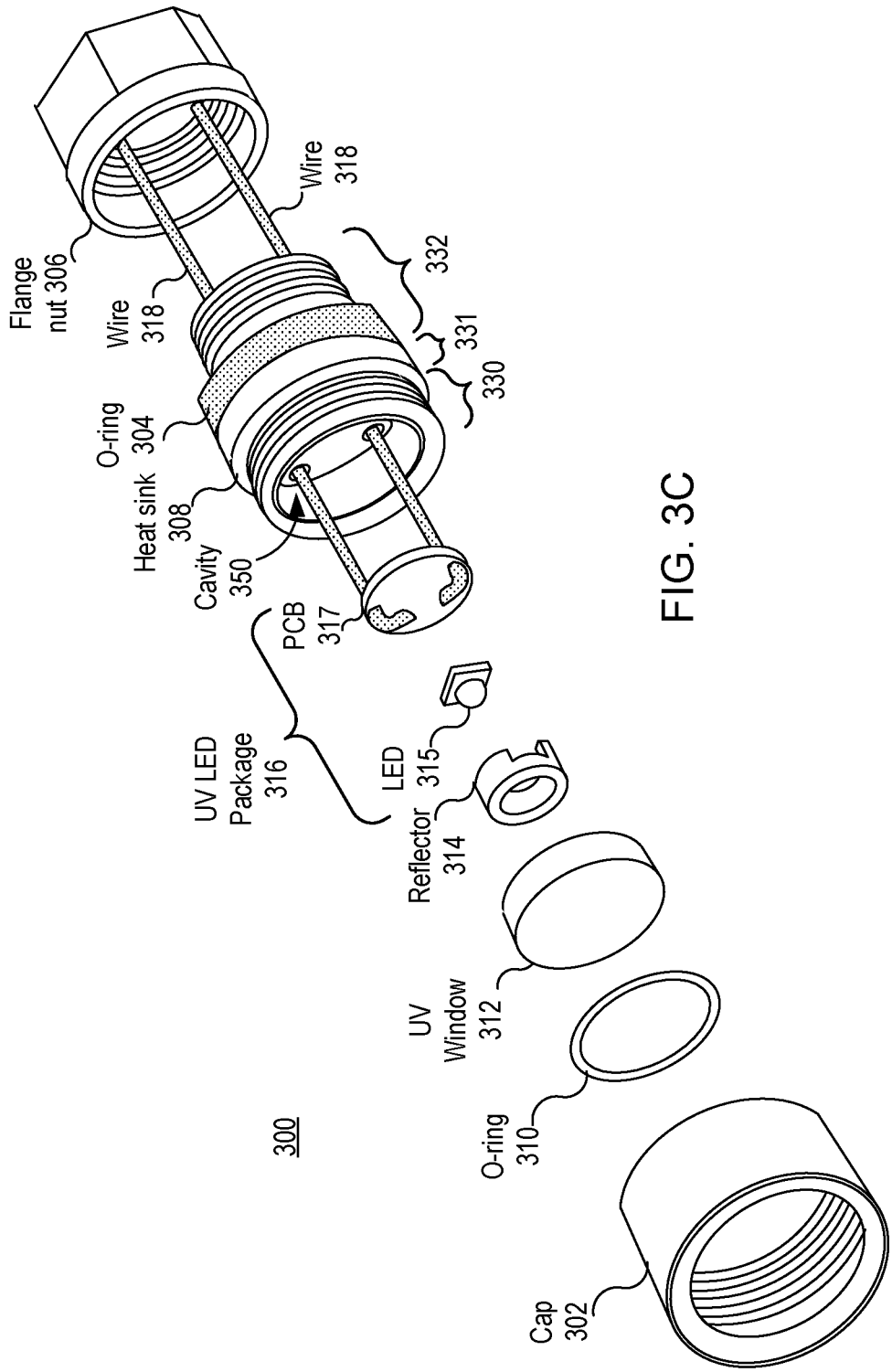
FIG. 3C shows an exploded perspective view of the UV disinfection device in FIG. 3A.

FIG. 3A shows a side view of a UV disinfection device 300 according to embodiments of the present disclosure. FIG. 3B shows a cross sectional view of the UV disinfection device 300 in FIG. 3A. FIG. 3C shows an exploded perspective view of the UV disinfection device in FIG. 3A. As depicted, the UV disinfection device 300, which may be similar to the device 106, may include: a cap 302 having a hollow cylindrical body and an inner lip disposed along a top inner rim of the body, the body including a first thread formed on an inner side surface of the body; and a heat sink 308 being substantially a hollow cylinder and a circular disk disposed inside the hollow cylinder and extending along a radial direction to thereby define an upper space (cavity) 350 and a lower space inside the hollow cylinder. The heat sink 308 may include an upper portion 330, a middle portion 331, and a lower portion 332, where the lower portion may have a smaller outer diameter than the middle portion to thereby define a shoulder 334 at the boundary between the lower and upper portions. The heat sink 308 may include a second thread that is formed on an outer side surface of the upper portion 330 and engages the first thread of the cap 302, a third thread that is formed on an outer side surface of the lower portion 332, and an o-ring groove that is formed on the top surface thereof.

In embodiments, the UV disinfection device 300 may also include: a UV light source package (such as UV LED package) 316 disposed inside the upper space (cavity) 350 of the heat sink 308 and generating UV light; a UV reflector 314 that reflects the UV light generated by the UV light source package 316; a first o-ring 310 seating on the o-ring groove formed in the heat sink 308; a UV window 312 disposed between an inner lip of the cap 302 and the first o-ring 310. When the heat sink 308 is secured into the cap 302 by engaging the first thread into the second threads, the heat sink 308 may compress the first o-ring against the bottom surface of the UV window 312 so that the first o-ring 310 may prevent the liquid from leaking into the upper space (cavity) 350 in the heat sink 308.

In embodiments, the UV disinfection device 300 may further include: a flange nut 306 having a fourth thread that engages the third thread formed in the lower portion 332 of the heat sink 308 and being hexagonal in shape; and a second o-ring 304 that seats on the shoulder 334 of the heat sink 308. To mount the device 300 on the wall of the container 102, the fourth thread of the flange nut 306 may be screwed into the third thread in the lower portion 332 of the heat sink 308. Also, upon turning the flange nut 306 relative to the heat sink 308, the second o-ring 304 may be compressed by the wall of the container 102 and the shoulder of the heat sink 308 so that the second o-ring may prevent the liquid from leaking through the gap between the device 300 and the wall of the container 102.

In embodiments, the heat sink 308 may dissipate the heat energy generated by the UV light source package 316. More specifically, a middle portion 331 of the heat sink 308 may be directly exposed to the liquid so that the heat energy generated by the UV light source package 316 may be directly discharged into the liquid. In embodiments, the heat sink 308 may be formed of material that has a high heat transfer coefficient, such as copper, stainless steel, aluminum, or other suitable metal. In embodiments, the cap 302 may be formed of metal, such as copper, stainless steel, and aluminum. In embodiments, the flange nut 306 may be formed of metal, such as copper, stainless steel, and aluminum.

In embodiments, the UV reflector 314 may reflect the UV light from the UV light source package 316 so that the UV light may be steered toward the liquid. In embodiments, the UV reflector 314 may be formed of highly reflective material, such as aluminum, or the inner surface of the UV reflector 314 may be coated with a reflecting material.

In embodiments, the UV window 312 may be formed of material, such as quartz, fused silica, or sapphire, that is transparent to the UV light generated by the UV light source package 316.

In embodiments, the UV light source package 316 may include a printed circuit board (PCB) 317 and a light emitting diode (LED) 315 mounted on the PCB. In embodiments, a pair of electrical wires 318 may be electrically coupled to the PCB 317 so that the electrical signals may be transmitted to the PCB 317 from outside the device 300. It should be apparent to those of ordinary skill in the art that the UV light source package 316 may include a suitable light source other than the LED 315.

It is noted that the UV disinfection device 300 has two o-rings (sealing mechanism) that ensure a tight liquid proof seal while a portion of the device is submerged in the liquid. In embodiments, the o-ring 310 may prevent the liquid from leaking into the cavity 350, i.e., it may protect the electrical circuit of the UV light source package 316 from damages by the liquid.

In embodiments, a portion of the heat energy generated by the UV light source package 316 may be directly discharged into the liquid by the heat sink 308. Also, a portion of the heat energy generated by the UV light source package 316 may be transferred from the heat sink 308 to the cap 302, and the cap 302 may in turn discharged the heat energy into the liquid. Furthermore, in embodiments, the heat energy generated by the UV light source package 216 may be transferred from the heat sink 308 to the flange nut 306, and the flange nut 306 may also discharge the heat energy to the container 102 or ambient atmosphere. As such, in embodiments, the cooling mechanism may protect the device from thermal damages, allowing application of the device 300 to high power disinfections.

In general, the direct contact between the liquid and the device 300 may lead to fouling of the UV window 312 and, thus, the device 300 may need to be easily mounted to and dismounted from the container 102 for maintenance purposes. In embodiments, the UV disinfection device 300 may be mounted to and dismounted from the wall of the container 102 by simply turning the flange nut 306 relative to the heat sink 308, reducing the effort for maintenance of the device 300. In embodiments, the outer diameter of the cap 302 may be about 13 mm.

Figure 4C:
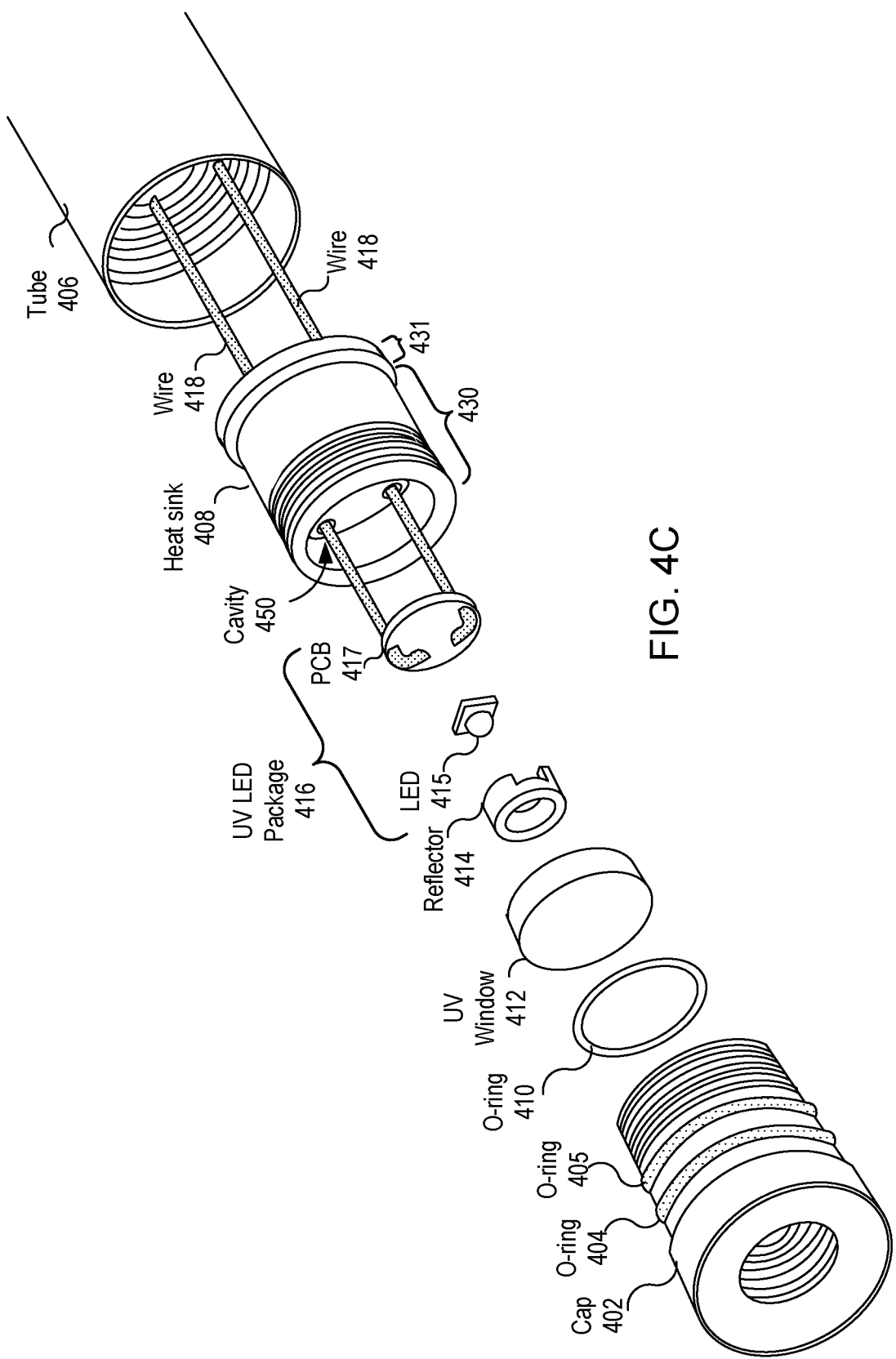
FIG. 4C shows an exploded perspective view of the UV disinfection device in FIG. 4A.

FIG. 4A shows a side view of a UV disinfection device 400 according to embodiments of the present disclosure. FIG. 4B shows a cross sectional view of the UV disinfection device 400 in FIG. 4A. FIG. 4C shows an exploded perspective view of the UV disinfection device in FIG. 4A. As depicted, the UV disinfection device 400 may include: a cap 402 having a hollow cylindrical body and an inner lip that is disposed along a top inner rim of the body and includes a first o-ring groove, the body including a first thread formed on an inner side surface of the body, a second thread formed on an outer side surface of the body, and second and third o-ring grooves formed on an outer side surface of the body; and a heat sink 408 being substantially a hollow cylinder and a circular disk disposed inside the hollow cylinder and extending along a radial direction to thereby define an upper space (cavity) 450 and a lower space inside the hollow cylinder. The heat sink 408 may include a lower portion 431, an upper portion 430 that is disposed inside the cap 402, and a third thread that is formed on the outer side surface of the upper portion and engages the first thread of the cap 402. The device 400 may also include: a UV light source package (such as UV LED package) 416 disposed inside the cavity 450 of the heat sink 408 and generating UV light; a UV reflector 414 that reflects the UV light generated by the UV light source package 416; a first o-ring 410 seating on the first o-ring groove of the cap 402; a UV window 412 disposed between the first o-ring 410 and the heat sink 408. When the heat sink 408 is secured into the cap 402 by engaging the second thread into the first thread, the heat sink 408 may compress the first o-ring against the top surface of the UV window 412 so that the first o-ring 410 may prevent the liquid from leaking into the cavity 450.

In embodiments, the UV disinfection device 400 may further include: a tube 406 having a fourth thread that engages the second thread of the cap 402; and a second o-ring 404 and a third o-ring 405 seating on the second and third o-ring grooves of the cap 402, respectively. When the tube 406 is tightened onto the third thread of the cap 402, the inner side surface of the tube 406 may compress the second and third o-rings 404 and 405 to prevent the liquid from leaking into the tube 406.

In embodiments, the heat sink 408 may dissipate the heat energy generated by the UV light source package 416, i.e., the heat sink 408 may transfer the heat energy from the UV light source package 416 to the cap 402, and the cap 402 in turn may transfer the heat energy to the liquid and the tube 406. In embodiments, the tube 406 in turn discharge the heat energy into liquid or ambient atmosphere, depending on whether the tube is submerged in the liquid or not. In embodiments, the heat sink 408 may be formed of material that has a high heat transfer coefficient, such as copper, stainless steel, aluminum, or other suitable metal. In embodiments, the cap 402 may be formed of metal, such as copper, stainless steel, and aluminum. In embodiments, the tube 406 may be formed of metal, such as copper, stainless steel, and aluminum.

In embodiments, the UV reflector 414 may reflect the UV light from the UV light source package 416 so that the UV light may be steered toward the liquid. In embodiments, the UV reflector 414 may be formed of highly reflective material, such as aluminum, or the inner surface of the UV reflector 414 may be coated with a reflecting material.

In embodiments, the UV window 412 may be formed of material, such as quartz, fused silica, or sapphire, that is transparent to the UV light generated by the UV light source package 416.

In embodiments, the UV light source package 416 may include a printed circuit board (PCB) 417 and a light emitting diode (LED) 415 mounted on the PCB. In embodiments, a pair of electrical wires 418 may be electrically coupled to the PCB 417 so that the electrical signals may be transmitted to the PCB 417 from outside the device 400. It should be apparent to those of ordinary skill in the art that the UV light source package 416 may include a suitable light source other than the LED 415.

It is noted that the UV disinfection device 400 has three o-rings (sealing mechanisms) 404, 405, and 410 that ensure a tight liquid proof seal while a portion of the device is submersed in the liquid. In embodiments, the first o-ring 410 may prevent the liquid from leaking into the cavity 450, i.e., it may protect the electrical circuit of the UV light source package 416 from damages by the liquid.

In embodiments, the heat energy generated by the UV light source package 416 may be discharged into the liquid by the heat sink 408 via the tube 406 and cap 402. As such, in embodiments, the cooling mechanism may protect the device from thermal damages, allowing application of the device 400 to high power disinfections.

In embodiments, the device 400 may be used to disinfect an area where the UV light from other UV light sources may not be reached. For instance, the UV light sources 104 and 106 on the container 102 may be arranged such that the UV light may not reach some areas in the container, such as the bottom corners of the container 102. In such a case, the user may use the device 400 to disinfect the liquid in the corners by submerging the device 400 in the liquid and pointing the UV light toward the corners. In embodiments, multiple tubes 406 with different lengths may be used, depending on the depth of the areas to be disinfected from the liquid surface.

Figures 5A, 5B:
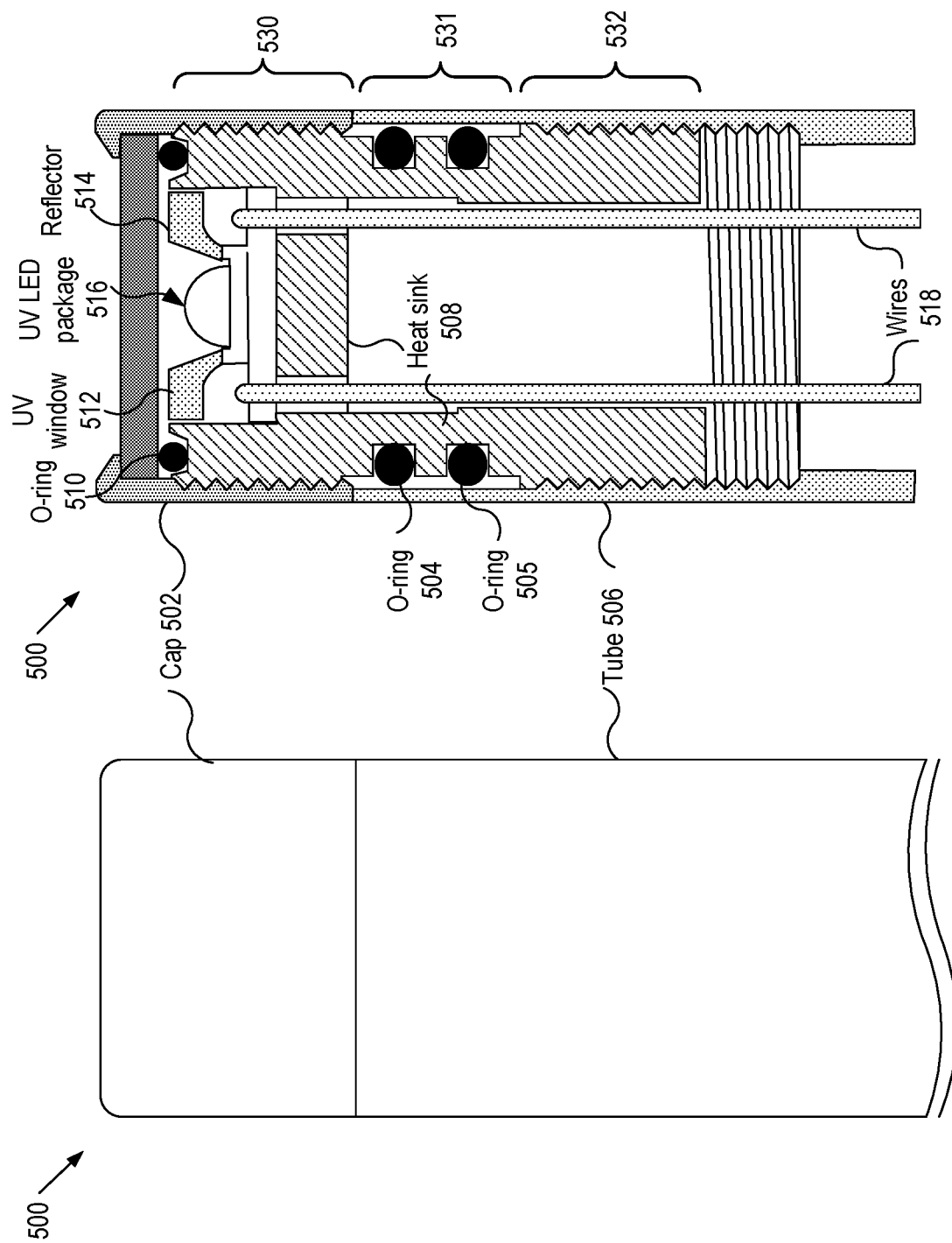
FIG. 5A shows a side view of a UV disinfection device according to embodiments of the present disclosure.
FIG. 5B shows a cross sectional view of the UV disinfection device in FIG. 5A.
Figure 5C:
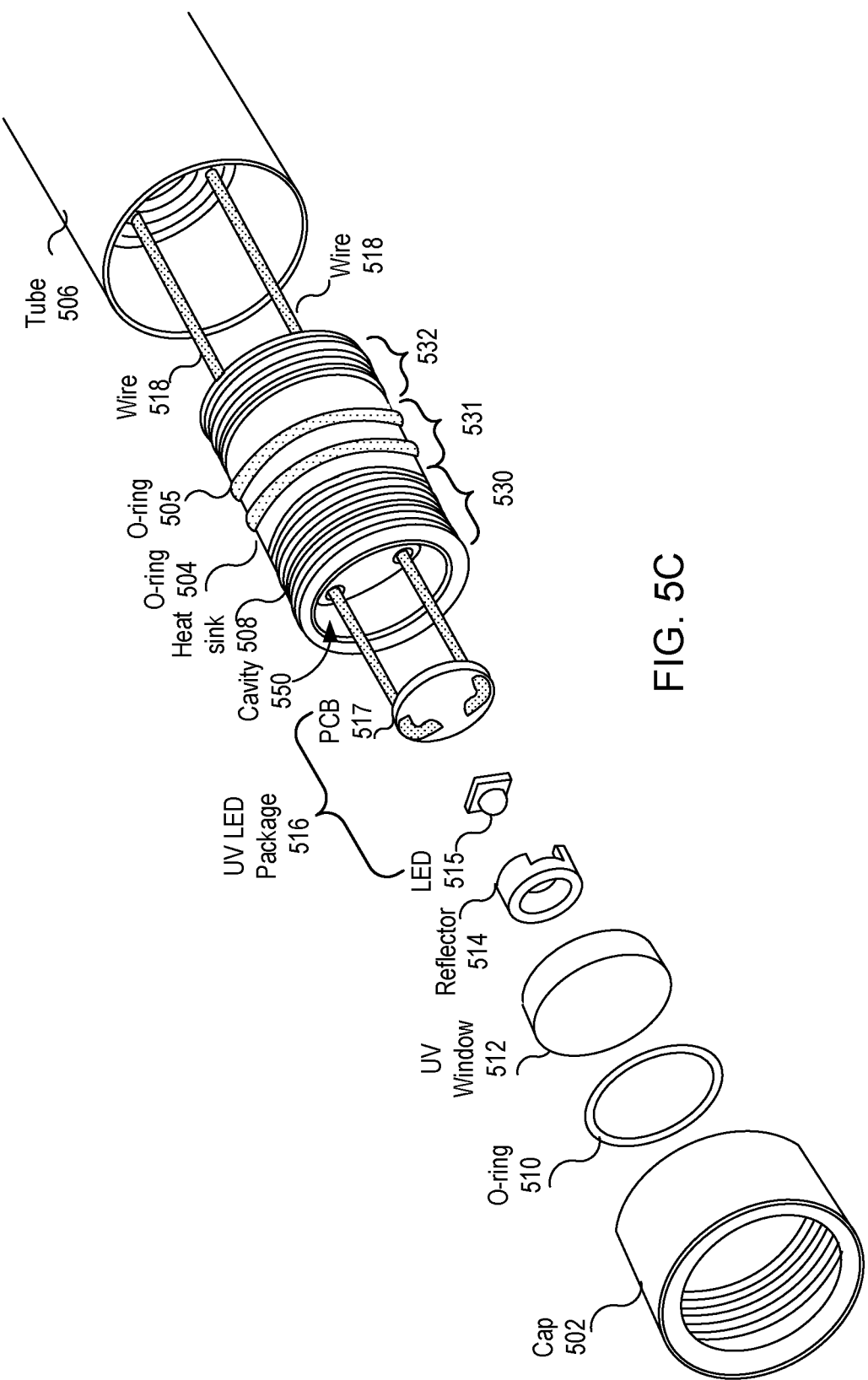
FIG. 5C shows an exploded perspective view of the UV disinfection device in FIG. 5A.

FIG. 5A shows a side view of a UV disinfection device 500 according to embodiments of the present disclosure. FIG. 5B shows a cross sectional view of the UV disinfection device 500 in FIG. 5A. FIG. 5C shows an exploded perspective view of the UV disinfection device in FIG. 5A. As depicted, the UV disinfection device 500 may include: a cap 502 having a hollow cylindrical body and an inner lip that is disposed along a top inner rim of the body, the body including a first thread formed on an inner side surface of the body; and a heat sink 508 being substantially a hollow cylinder that includes an upper portion 530, a middle portion 531, and a lower portion 532. The heat sink 508 may include a circular disk disposed inside the hollow cylinder and extending along a radial direction to thereby define an upper space (cavity) 550 and a lower space inside the hollow cylinder. The heat sink 508 may further include: a first o-ring groove that is formed on the top surface thereof; second and third o-ring grooves formed on the outer side surface of the middle portion 532; and second and third threads that are formed on the outer side surfaces of the upper and lower portions 530 and 532, respectively, where the second thread engages the first thread of the cap 510.

The device 500 may also include: a UV light source package (such as UV LED package) 516 disposed inside the cavity 550 of the heat sink 508 and generating UV light; a UV reflector 514 that reflects the UV light generated by the UV light source package 516; first, second, and third o-rings 510, 504, and 505 seating on the first, second and third o-ring grooves of the heat sink 508, respectively; a UV window 512 disposed between an inner lip of the cap 502 and the first o-ring 510. When the heat sink 508 is secured into the cap 502 by engaging the second thread into the first thread, the heat sink 508 may compress the first o-ring 510 against the bottom surface of the UV window 512 so that the first o-ring 510 may prevent the liquid from leaking into the cavity 550.

In embodiments, the UV disinfection device 500 may further include a tube 506 having a fourth thread that engages the third thread of the heat sink 508. When the tube 506 is tightened onto the third thread of the heat sink 508, the inner surface of the tube 506 may compress the second and third o-rings 504 and 505 to prevent the liquid from leaking into the tube 506.

In embodiments, the heat sink 508 may dissipate the heat energy generated by the UV light source package 516, i.e., the heat sink 508 may transfer the heat energy from the UV light source package 516 to the cap 502, and the cap 502 in turn may discharge the heat energy into the liquid. In embodiments, the tube 506 in turn discharge the heat energy into liquid or ambient atmosphere, depending on whether the tube is submerged in the liquid or not. In embodiments, the heat sink 508 may be formed of material that has a high heat transfer coefficient, such as copper, stainless steel, aluminum, or other suitable metal. In embodiments, the cap 502 may be formed of metal, such as copper, stainless steel, and aluminum. In embodiments, the tube 506 may be formed of metal, such as copper, stainless steel, and aluminum.

In embodiments, the UV reflector 514 may reflect the UV light from the UV light source package 516 so that the UV light may be steered toward the liquid. In embodiments, the UV reflector 514 may be formed of highly reflective material, such as aluminum, or the inner surface of the UV reflector 514 may be coated with a reflecting material.

In embodiments, the UV window 512 may be formed of material, such as quartz, fused silica, or sapphire, that is transparent to the UV light generated by the UV light source package 516.

In embodiments, the UV light source package 516 may include a printed circuit board (PCB) 517 and a light emitting diode (LED) 515 mounted on the PCB. In embodiments, a pair of electrical wires 518 may be electrically coupled to the PCB 517 so that the electrical signals may be transmitted to the PCB 517 from outside the device 500. It should be apparent to those of ordinary skill in the art that the UV light source package 516 may include a suitable light source other than the LED 515.

It is noted that the UV disinfection device 500 has three o-rings (sealing mechanisms) 504, 505, and 510 that ensure a tight liquid proof seal while a portion of the device is submerged in the liquid. In embodiments, the first o-ring 510 may prevent the liquid from leaking into the cavity 550, i.e., it may protect the electrical circuit of the UV light source package 516 from damages by the liquid.

In embodiments, the heat energy generated by the UV light source package 516 may be discharged into the liquid and/or ambient atmosphere by the heat sink 508 via the tube 506 and cap 502. As such, in embodiments, the cooling mechanism may protect the device from thermal damages, allowing application of the device 500 to high power disinfections.

In embodiments, the device 500 may be used to disinfect an area where the UV light from other UV light sources may not be reached. For instance, the UV light sources 104 and 106 on the container 102 may be arranged such that the UV light may not reach some areas, such as the bottom corners of the container 102. In such a case, the user may use the device 500 to disinfect the liquid in the corners by submerging the device 500 in the liquid and pointing the UV light toward the corners. In embodiments, multiple tubes 506 with different lengths may be used, depending on the depth of the area from the liquid surface to be disinfected. It is noted that the devices in FIGS. 1A-5C may be used to disinfect both liquid and gas, where the term fluid collectively refers to both liquid and gas.

While the invention is susceptible to various modifications and alternative forms, specific examples thereof have been shown in the drawings and are herein described in detail. It should be understood, however, that the invention is not to be limited to the particular forms disclosed, but to the contrary, the invention is to cover all modifications, equivalents, and alternatives falling within the scope of the appended claims.

What is claimed is:

1. An apparatus for disinfecting fluid, comprising:
 a pipe having first and second linear segments and an elbow that is removably secured to the first and second linear segments;
 one or more disinfection devices installed on the elbow to be submersible in fluid, each of the one or more disinfection devices being configured to generate light for disinfecting fluid in a linear segment of the pipe;
 a laminar flow enforcer installed inside the first segment of the pipe and configured to generate a laminar flow in the first segment of the pipe; and
 an orifice installed inside the first segment of the pipe and having an opening so that an entire flow flowing through the first segment of the pipe exits the opening as one laminar flow pillar,
 wherein a diameter of the laminar flow pillar is smaller than an inner diameter of the pipe thereby forming an air gap between the laminar flow pillar and the first segment of the pipe to thereby separate the laminar flow pillar from an inner surface of the first segment of the pipe,
 wherein the one or more disinfection devices are located at a downstream end of the laminar flow pillar and transmits the light to a substantially upstream direction of the laminar flow pillar, and
 wherein a portion of the light for disinfecting fluid is internally reflected at an interface between the laminar flow pillar and the air gap within the first segment of the pipe, sufficient to disinfect the fluid in the laminar flow pillar.

2. The apparatus of claim 1, wherein the pipe includes multiple bending points to form multiple steps.

3. The apparatus of claim 1, wherein the pipe includes multiple bending points to have a spiral shape.

4. The apparatus of claim 1, wherein the laminar flow enforcer includes one or more tubes that have smaller diameters than the pipe and extend along a longitudinal direction of the pipe.

5. The apparatus of claim 1, wherein the light for disinfecting fluid propagates substantially parallel to the linear segment of the pipe.

6. The apparatus of claim 1, further comprising:
 a turbulence remover for reducing turbulence in fluid.

7. The apparatus of claim 1, wherein at least one of the one or more disinfection devices includes an ultraviolet light emitting diode (UV LED) that generates the light for disinfection fluid.

8. The apparatus of claim 1, wherein at least one of the one or more disinfection devices comprises:
 a cap having a hollow cylindrical body;
 a heat sink including a cavity therein, at least a portion of the heat sink being disposed inside the cap and detachably secured to the cap;
 a light source package disposed inside the cavity of the heat sink and configured to generate the light for disinfecting fluid;
 a window disposed on the heat sink and formed of material that passes through the light for disinfecting fluid generated by the light source package;
 a nut disposed outside the heat sink and detachably secured to the cap; and
 a sealing mechanism for preventing liquid from leaking into the cavity;
 wherein the heat sink is configured to transfer heat energy generated by the light source package to the cap and the nut.

9. The apparatus of claim 1, wherein at least one of the one or more disinfection devices comprises:
 a cap having a hollow cylindrical body;
 a heat sink having an upper portion that is disposed inside the cap, is detachably secured to the cap, and includes a cavity therein;
 a light source package disposed inside the cavity of the heat sink and configured to generate the light for disinfecting fluid;
 a window disposed on the heat sink and formed of material that passes through the light for disinfecting fluid generated by the light source package;
 a tube disposed outside of the cap and detachably secured to the cap; and
 a sealing mechanism for preventing liquid from leaking into the cavity;
 wherein the heat sink is configured to transfer heat energy generated by the light source package to the cap and the tube.

* * * * *